(12) United States Patent
Yufa

(10) Patent No.: US 6,346,983 B1
(45) Date of Patent: Feb. 12, 2002

(54) METHODS AND WIRELESS COMMUNICATING PARTICLE COUNTING AND MEASURING APPARATUS

(76) Inventor: Aleksandr L. Yufa, P.O. Box 1677, Colton, CA (US) 92324

(*) Notice: Subject to any disclaimer, the term of this patent is extended or adjusted under 35 U.S.C. 154(b) by 0 days.

(21) Appl. No.: 09/015,458

(22) Filed: Jan. 29, 1998

(51) Int. Cl.[7] .............................................. G01N 21/53
(52) U.S. Cl. ..................................... 356/338; 356/338
(58) Field of Search ................................ 356/336, 338, 356/339, 437, 438, 439

(56) References Cited

U.S. PATENT DOCUMENTS

| | | | |
|---|---|---|---|
| 4,160,246 A | * 7/1979 | Martin et al. ................. | 356/438 |
| 4,798,465 A | 1/1989 | Knollenberg ................. | 356/73 |
| 5,524,129 A | 6/1996 | Pettigrew ..................... | 377/6 |
| 5,751,424 A | * 5/1998 | Bostater ........................ | 356/342 |

* cited by examiner

Primary Examiner—Richard A. Rosenberger

(57) ABSTRACT

An improved methods and apparatus for particle counting and measuring provide the counting and measuring of the airborne (gas) particle and/or liquid contamination and include a remote sensor 5, wireless communicating with a data processing and control system 13, comprising a microprocessor system 27 and a wireless communication means 56, comprising a transmitting-receiving means 58 connected to an aerial means 57. The sensor system 5 includes a particle detecting system 4, providing the sensing a light created by an intersection of the particles with a light beam within particle monitoring region of the particle detecting system 4, particle detection and timing processing of the detected signals, and a wireless communication means 36 intended for wireless communication with the data processing and control system 13, providing a received data processing, illuminating of the resulting information and also providing a wireless communicating control of the sensor 5.

8 Claims, 9 Drawing Sheets

METHODS AND WIRELESS COMMUNICATING PARTICLE COUNTING AND MEASURING APPARATUS

FIELD OF THE INVENTION

This invention relates to air, gas and liquid quality and, more particularly, to devices, apparatus and instruments for airborne (gas) particle and/or liquid contamination quantity counting and particle size measuring by light (laser) beam.

BACKGROUND OF THE INVENTION

The methods and devices for determining quantity and size of the particles and/or liquid (water) contaminations are now well known, and it is also well known that powerful light or laser and detecting system can be, and have been used to achieve particle size and particle quantity measurements. Such devices, mostly using or computers, are well known and described, for example, in the articles: R. G. Knollenberg, B. Schuster—"Detection and Sizing of Small Particles in Open Cavity Gas Laser," Applied Optics, Vo. 11, No. 7, November 1972, pp. 1515–1520; R. G. Knollenberg—"An Active Scattering Aerosol Spectrometer," Atmospheric Technology, No. 2, June 1973, pp. 80–81; Schehl, Ergun, Headrick—"Size Spectrometry of Aerosols Using Light Scattering from the Cavity of a Gas Laser," Review of Scientific Instruments, Vol. 44, No. 9, September 1973; R. G. Knollenberg—"Active Scattering Aerosol Spectrometry," National Bureau of Standards Special Publication, No. 412, October 1974, pp. 57–64; R. G. Knollenberg, R. E. Luehr—"Open Cavity Laser Active Scattering Particle Spectrometry from 0.05 to 5.0 Microns," Fine Particles, Aerosol Generation Measurement, Sampling and Analysis, Academic Press, May 1975, pp. 669–696; R. G. Knollenberg—"Three New Instruments for Cloud Physics Measurements: The 2-D Spectrometer, the Forward Scattering Spectrometer Probe, and the Active Scattering Aerosol Spectrometer," American Meteorological Society, International Conference on Cloud Physics, July 1976, pp. 554–561; R. G. Knollenberg—"The Use of Low Power Laser in Particle Size Spectrometry", Proceeding of the Society of Photo-Optical Instrumentation Engineers, Practical Applications of Low Power Lasers, Vo. 92, August 1976, pp. 137–152; Elterman—"Brewster Angle Light Trap," Applied Optics, Vol. 16, No. 9, September 1977; Marple—"The Aerodynamics Size Calibration of Optical Particle Counters by Inertial Impactors," Aerosol Measurement, 1979; Diehl, Smith, Sydor—"Analysis by Suspended Solids by Single-Particle Scattering," Applied Optics, Vol. 18, No. 10, May 1979; K. Suda—Review of Scientific Instruments, Vol. 51, No. 8, August 1980, pp. 1049–1058; R. G. Knollenberg—"The Measurement of Particle Sizes Below 0.1 Micrometers", Journal of Environment Science, January–February, 1985, pp. 64–67; Peters—"20 Good Reasons to Use In Situ Particle Monitors", Semiconductor International, Nov. 1992, pp. 52–57 and Busselman et al.—"In Situ Particle Monitoring in a Single Wafer Poly Silicon and Silicon Nitride Etch System", IEEE/SEMI Int'l Semiconductor Manufacturing Science Symposium, 1993, pp. 20–26.

The reference in these articles is made to the devices and methods of particle measurement, utilizing an open cavity laser for particle detection.

The known devices, having the particle detecting means are based on the scattered light collection, as it is mentioned, for example, in U.S. Pat. No. 4,140,395, U.S. Pat. No. 4,798,465, U.S. Pat. No. 5,467,189 and in 5,515,164 of the prior art.

For example, in U.S. Pat. No. 4,140,395 and in U.S. Pat. No. 4,798,465 of the prior art are used the imaging systems, which are based on lenses.

Yet in other prior art (for example, such as U.S. Pat. No. 5,467,189 and U.S. Pat. No. 5,515,164) we can find the devices (sensors) with ellipsoidal mirrors instead of the lens systems or non-divergent quadric mirrors.

All these devices, mentioned in the prior art above, use light scattering focalizing methods. Such methods are based on the collection of the scattered light. A light scattering occurs at the first focal point (focus) by intersecting. Considering stochastic processes of the light scattering, the devices, mentioned in the above prior art, use mirrors or optics. This is necessary for scattered light, collecting and focalizing at the second focal point (focus), where a light detector is placed and intended for scattered light detection.

Further the devices, based on scattered light collection and some other detection methods (for example, by light splitting), use a different variations of the comparison method for the particle size measuring. Such method can be illustrated (see FIG. 1), for example, by U.S. Pat. No. 4,798,465. On FIG. 1 is shown the particle size detection device, using one of the particle measuring comparison method variations. The signal from detectors 1 via the amplifiers 61 follow to the comparators 62, which is connected to the reference voltage means 63. The amplified detected signals are compared with the predetermined reference voltages for the particle size qualifying.

Such methods cannot provide light the sufficiently light the sensitivity related to the increasing requirements to the particle counting and measuring devices, because of the analog (amplitude) method of comparison.

Another and also important deficiency of all known particle analyzing devices is the use of the wire leads (cable) for the particle detecting means connection to the data processing means.

The devices, using the wire (cable) connection of the particle detecting, means to the data processing and control system, are presented by two styles of their configuration: a portable configuration of the particle analyzing device, which is an entire unit comprising particle detecting means (sensor) connected by short wires (short cable) to the microprocessor means, or a remote sensor configuration of the particle analyzing device, wherein, for example, the sensor and the data processing means are represented by two separated and remote of each other units connected by long wires (long cable).

On FIG. 2 is shown, for example, a device (see U.S. Pat. No. 5,524,129) with the wire (cable) connection 20 of the sensor 22 with the microprocessor (CPU) 24(12).

It is known, that all wire (cable) connections in electronic apparatus are a source of the electromagnetic noise, which can create a distortion of the signals. Also the portable devices require local operation with them and exactly in the place of the airborne particle or liquid (water) contaminations assaying. The devices with long cable connection between the remote sensor and the data processing means have a limited mobility, because of cable.

Other known devices by U.S. Pat. Nos. 4,160,246 and 5,751,424 intended for the smoke detection and liquid mixture, gas or solid medium analysis respectively. The smoke detector by U.S. Pat. No. 4,160,246 does not provide the counting and measuring of the particles in the specimen and uses the analog processing of the signals. The probe by U.S. Pat. No. 5,751,424 does not provide the analysis of the airborne particle. Also these devices use one-way wireless communication for the data transmission only and do not provide the wireless transmission of the control commands/signals (automatic modes of turn-on/turn-off, switching of the particle size counting scale, etc.), requiring the handle control of the remote unit.

For example, it is known, that integrated circuits (chips) and semiconductors have been produced in "clean rooms". The air in such "clean rooms" should be very well cleaned. The continuing tendencies of improvement in circuit integration and degree of microminiaturization require corresponding improvements of the environment in "clean rooms" and efficiency and sensitivity of the measuring devices. And now, as it is known, the sensitivity of the counting and measuring devices should be at least as small as 0.1 µm (Micron). Such rate requires minimum distortions in the data processing signals. Also the measurements should be done in the different places of the semiconductor production areas of "clean rooms" and sometimes in the areas, which could be difficult to approach. The same is regarding the pharmaceutical and biological industries, where is required the well condition of the environment.

Thus, the comparison method of the particle size measuring (an analog comparison of the detected signal amplitudes with the appropriate reference voltages) and the wire (cable) connections between the sensors (particle detecting means) and create an insufficient signal to noise ratio, thereby limiting the sensitivity and efficiency of the particle counting and measuring devices. Also such wire (cable) connection, using in the known particle counting and measuring devices with the known devices with the remote sensors, limits the mobility of the particle counting and measuring instruments. Another known system by U.S. Pat. No. 4,160,246, intended for the smoke detection, comprises an infrared radiation source, photodetector, the frequency filters, audio amplifiers, annunciator driver, a plurality of light-emitting diodes (LED) and a horn or buzzer. This device uses a wireless communication (from the smoke detector/transmitter to the receiver/annunciator). Such smoke detector system does not provide counting and measuring of the particles in the specimen Also the device by U.S. Pat. No. 4,160,246 provides the analog processing of the signals.

OBJECT AND ADVANTAGES OF THE INVENTION

Accordingly, several objects and advantages of the present invention are to provide an improved methods and apparatus for airborne (gas) particle and/or liquid (water) contamination analysis.

It is the object of the invention to provide an improved method and apparatus for increasing the sensitivity of the particle counting and measuring means.

It is another object of the invention to provide an improved methods and apparatus for increasing the efficiency of the analyzing processes and means.

It is yet another object of the invention to provide an improved method and apparatus for decreasing electromagnetic noises by the elimination of wire (cable) connection between particle detecting means (sensors) and data processing means.

It is still further an object of the invention to provide an improved method and apparatus for increasing the authenticity of the information about air or liquid (water) composition.

It is still another object of the invention to provide an improved method and apparatus for increasing the mobility, compactness and convenient placement possibility of the remote detecting means.

Still, further objects and advantages will become apparent from a consideration of the ensuing description accompanying drawings.

Figure 1:
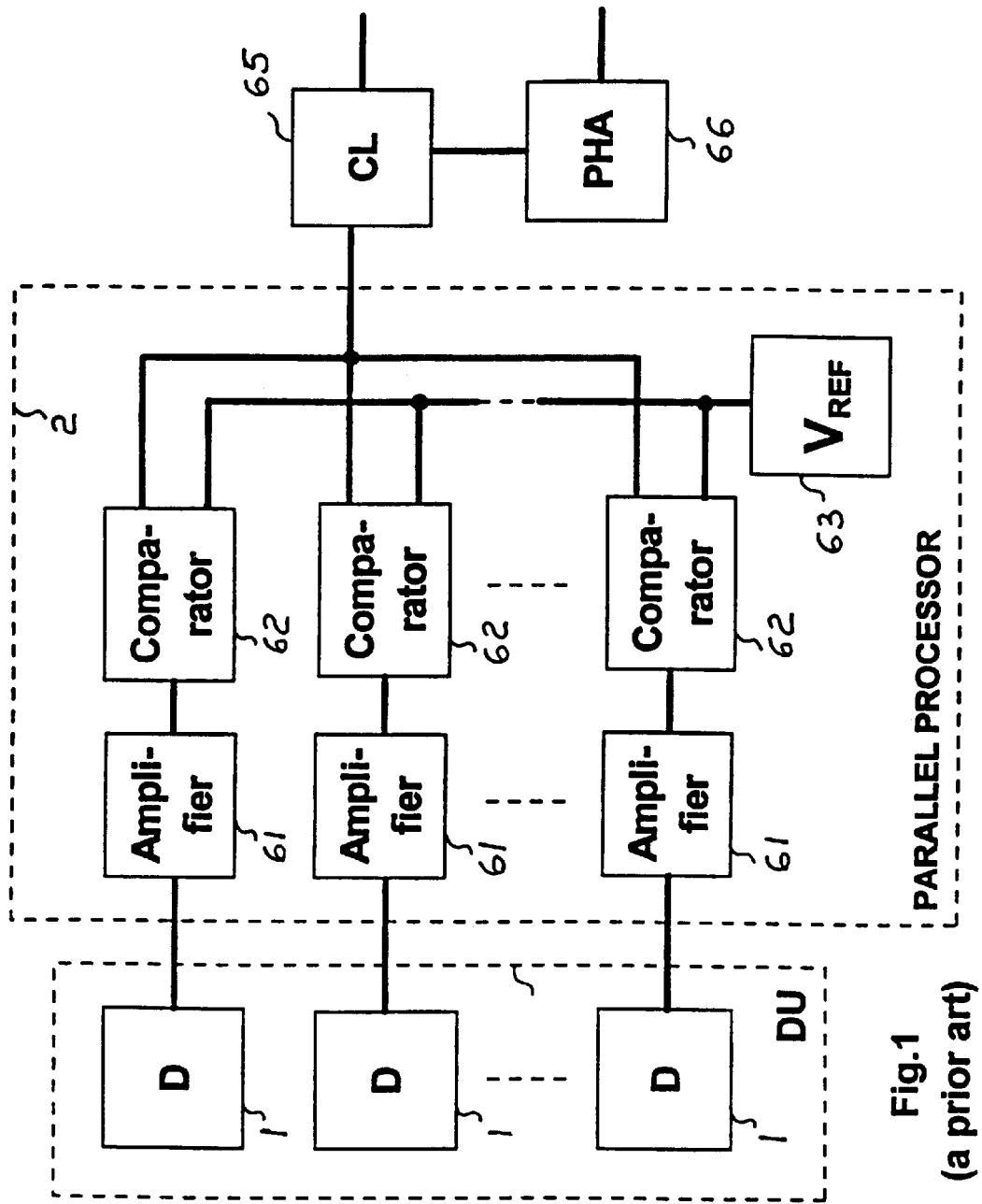
FIG. 1 is a presentation of the particle size detecting device (a prior art).

On FIG. 1 are shown: 1—the detectors (D); 60—a detection unit (DU); 61—the amplifiers; 62—the comparators; 63—a reference voltage means (VREF.); 65—a control logic; 66—a pulse height analyzer.

Figure 2:
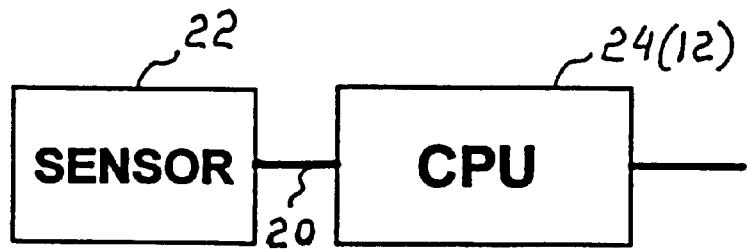
FIG. 2 is a presentation of portable counter (a prior art).

On FIG. 2 are shown: 35—a wire (cable); 75—a sensor; 76—a microprocessor (CPU).

Figure 3:
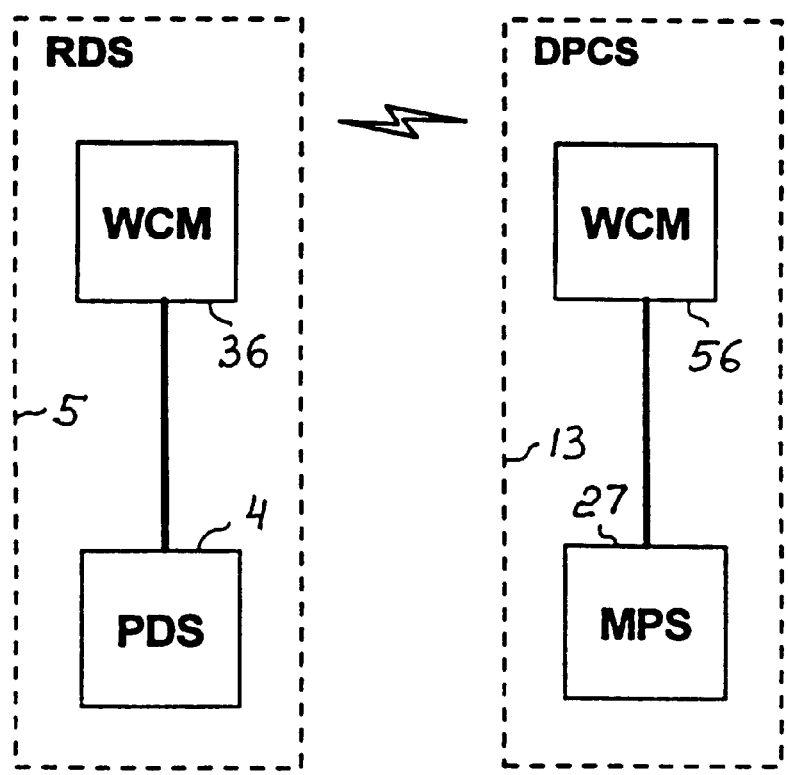
FIG. 3 is a presentation of the simplified structural schematic of an improved apparatus.

On FIG. 3 are shown: 4—a particle detecting system (PDS); 5—a remote detecting system (RDS); 13 a data processing and control system (DPCS); 27—a microprocessor system (MPS); 36—a wireless communication means (WCM) of the remote detecting system 5; 56—a wireless communication means (WCM) of the data processing and control system 13.

Figure 4:
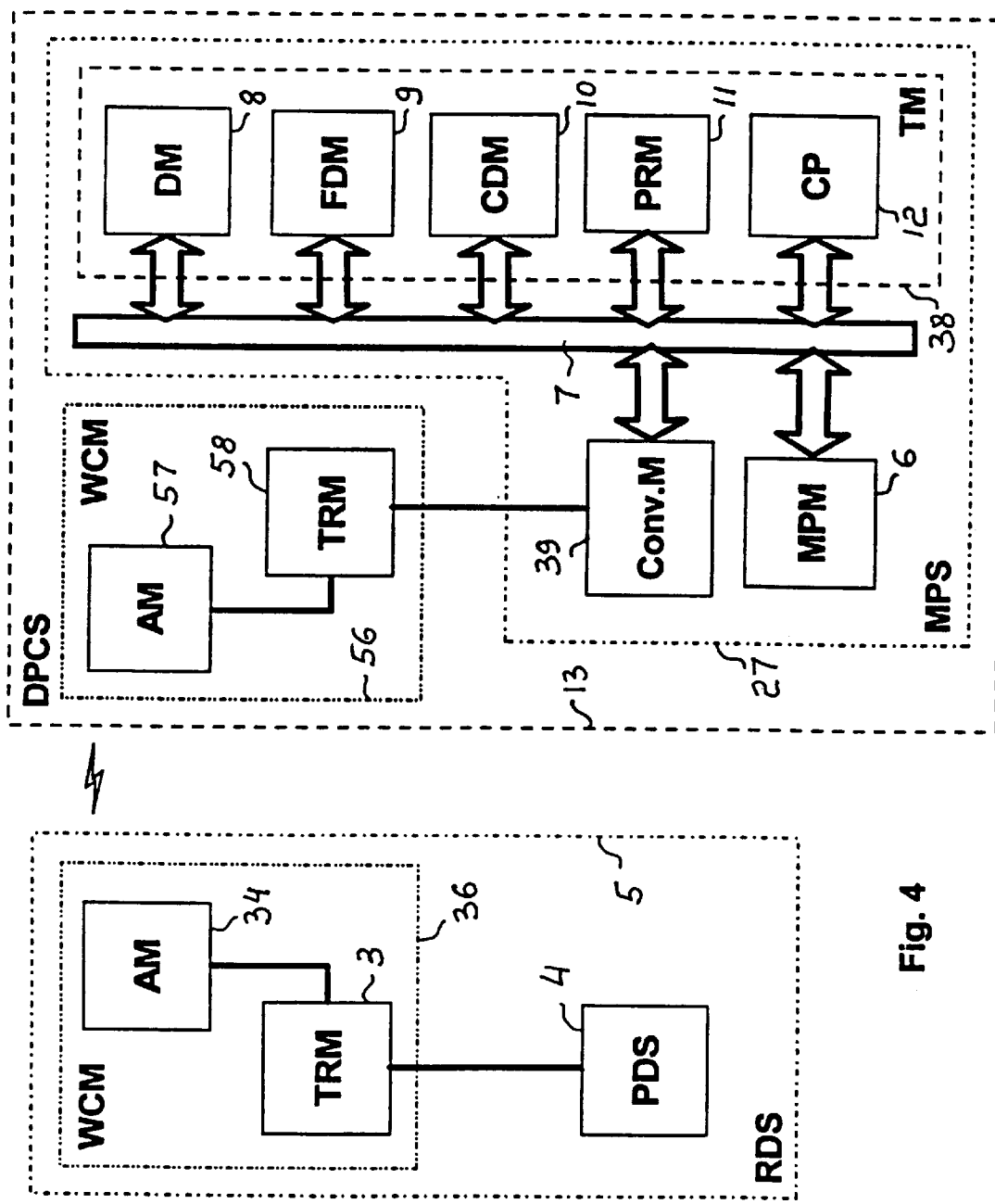
FIG. 4 is a presentation of the simplified detailed block-schematic of an improved apparatus.

On FIG. 4 are shown: 3—a transmitting-receiving means (TRM) of the wireless communication means 36; 4—a particle detecting system; 5—a remote detecting system; 6—a microprocessor means (MPM); 7—a multiplexed bus of the data processing and control system 13; 8—a displaying means (DM); 9—a floppy disk means (FDM); 10—a compact disk means (CDM); 11—a printing means (PRM); 12—a control panel (CP); 13—a data processing and control system; 27—a microprocessor system; 34—an aerial means (AM) of the wireless communication means 36; 36—a wireless communication means of the remote detecting system 5; 38—a terminal means (TM); 39—a conversion means (Conv.M) of the microprocessor system 27; 56—a wireless communication means of the data processing and control system 13; 57—an aerial means of the wireless communication means 56; 58—a transmitting—receiving means of the wireless communication means 56.

Figure 5:
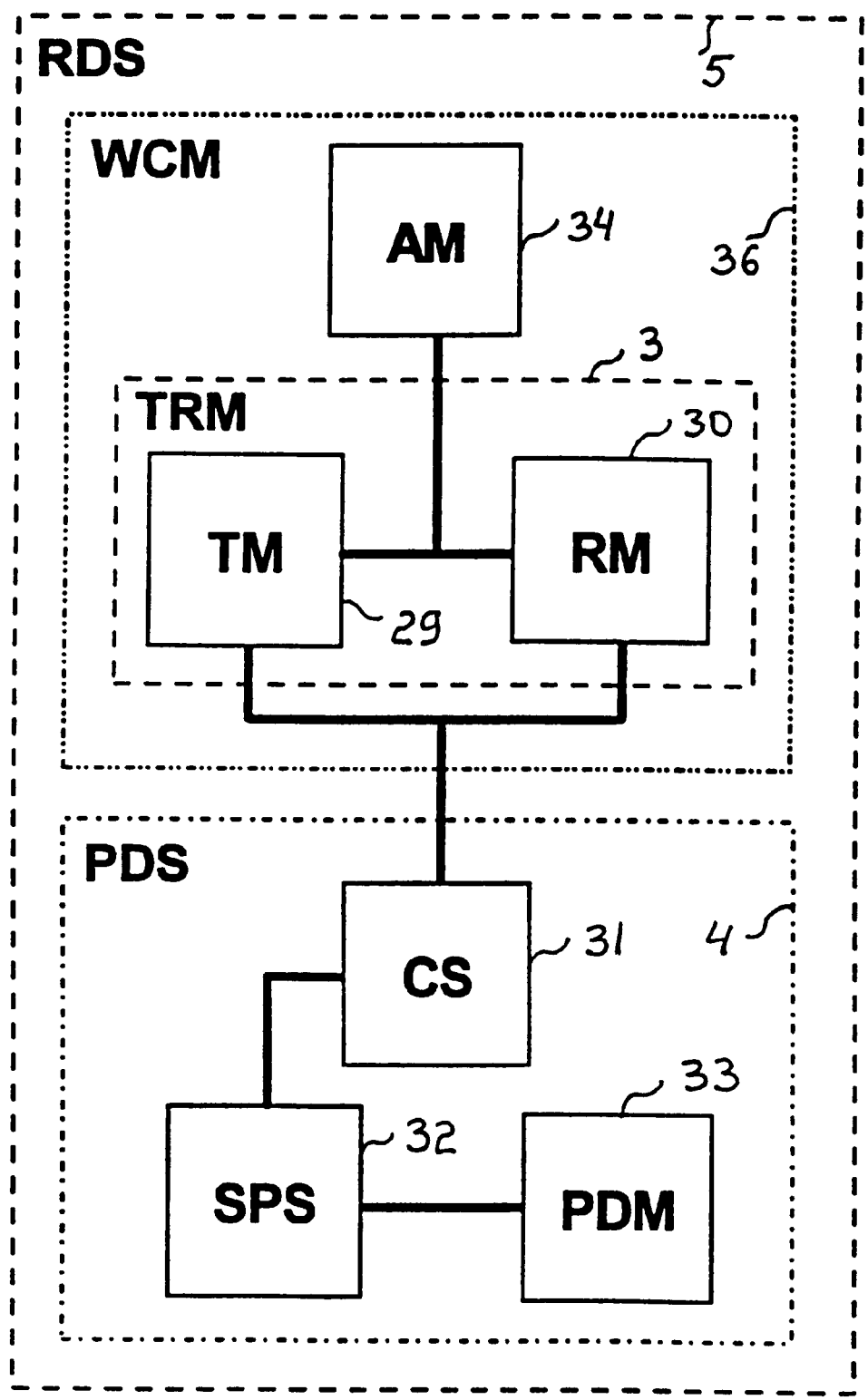
FIG. 5 is a presentation of the simplified block-schematic of the remote detecting system of an improved apparatus.

On FIG. 5 are shown: 3—a transmitting—receiving means of the wireless communication means 36; 4—a particle detecting system; 5—a remote detecting system; 29—a transmitting means (TM); 30—a receiving means (RM); 31—a conversion system (CS); 32—a signal processing system (SPS); 33—a particle detecting means (PDM); 34—an aerial means of the wireless communication means 36; 36—a wire less communication means of the remote detecting system 5.

Figure 6:
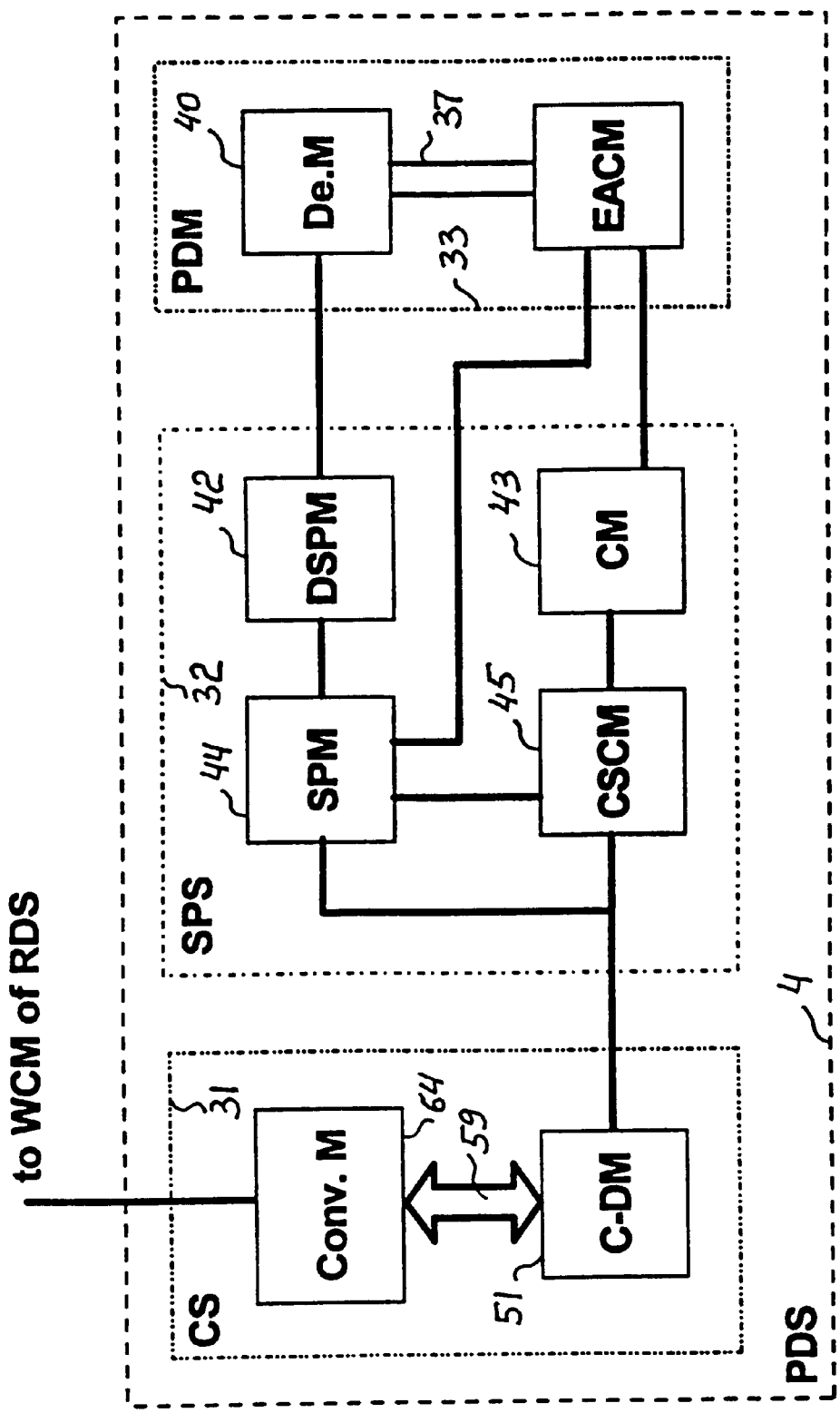
FIG. 6 is a presentation of the simplified block-schematic of the particle detecting system of an improved apparatus.

On FIG. 6 are shown: 31—a conversion system; 32—a signal processing system; 33—a particle detecting means; 37—a tubular means; 40—a detection means (De.M); 41—an environment assaying control means (EACM); 42—a detected ted signal processing means (DSPM); 43—a control means (CM); 44—a signal processing means (SPM); 45—a control signal conversion means (CSCM); 51—a coding-decoding means (C-DM); 59—a multiplexed bus of the remote detecting system 5; 64—a conversion means (Conv.M) of the conversion system 31.

Figure 7:
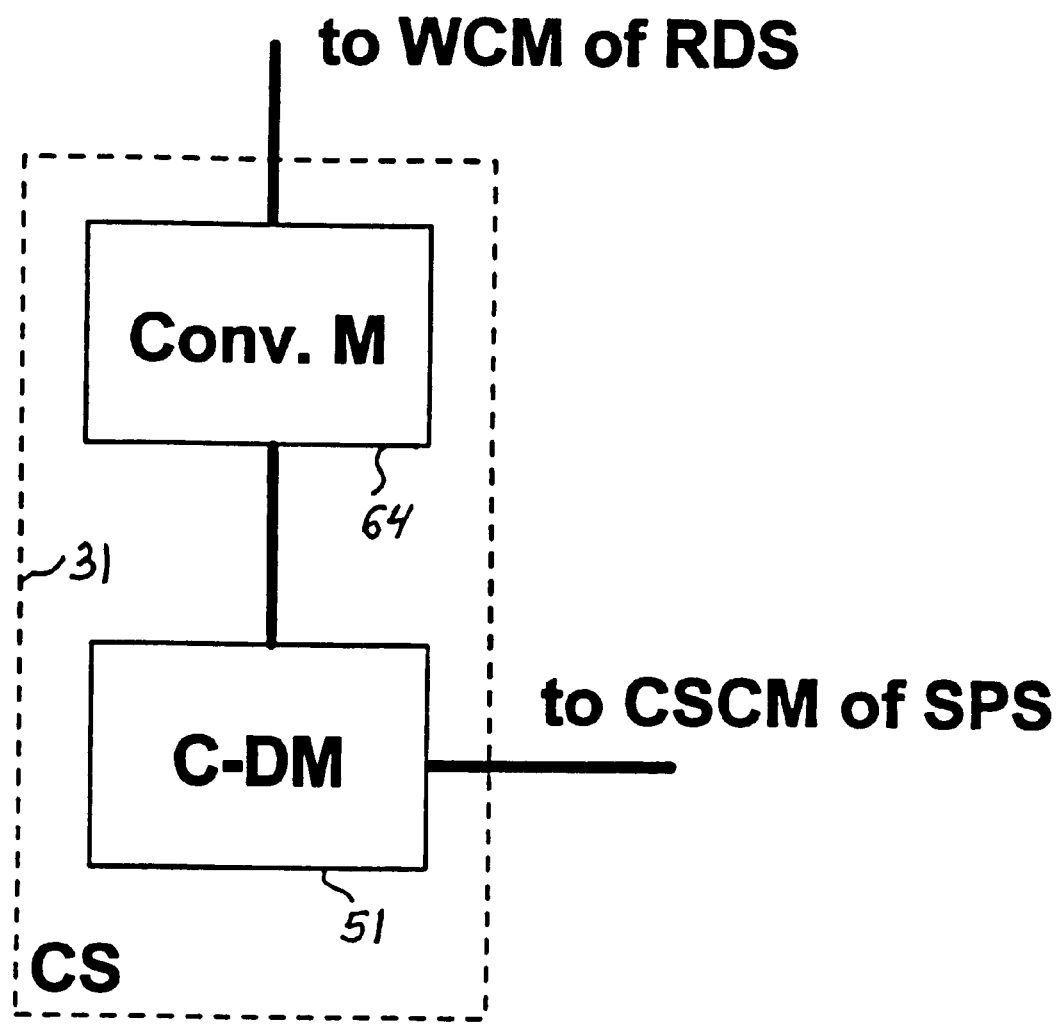
FIG. 7 is a presentation of the simplified block-schematic of the conversion system of an improved apparatus.

On FIG. 7 are shown: 31—a conversion system; 51—a coding-decoding means; 64—a conversion means of the conversion system 31.

Figure 8:
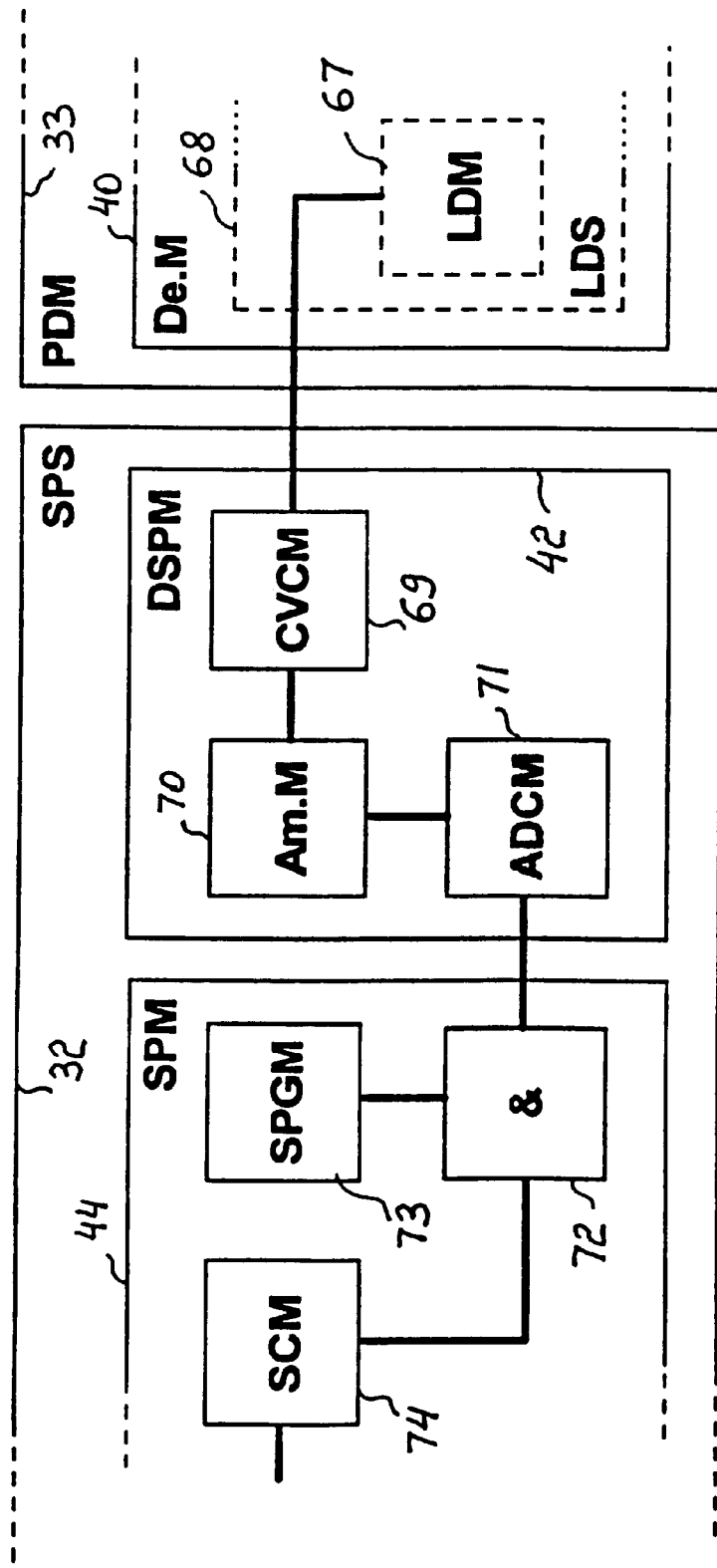
FIG. 8 is the presentation of the simplified block-schematic of an improved apparatus portion, providing a timing a strobing processes.

On FIG. 8 are shown: 32—signal processing system; 33—a particle detecting system; 40—a detection means; 42—a detected signal processing means; 44—a signal processing means; 67—a light detecting means (LDM); 68—a light detecting system (LDS); 69—a current-voltage conversion means (CVCM); 70—an amplifying means (Am.M); 71—an analog digital form pulse duration conversion means (ADCM); 72—a conjunction means (&); 73—a strobe pulse generating means (SPGM); 74—a selecting, sorting and counting means (SCM).

Figure 10:
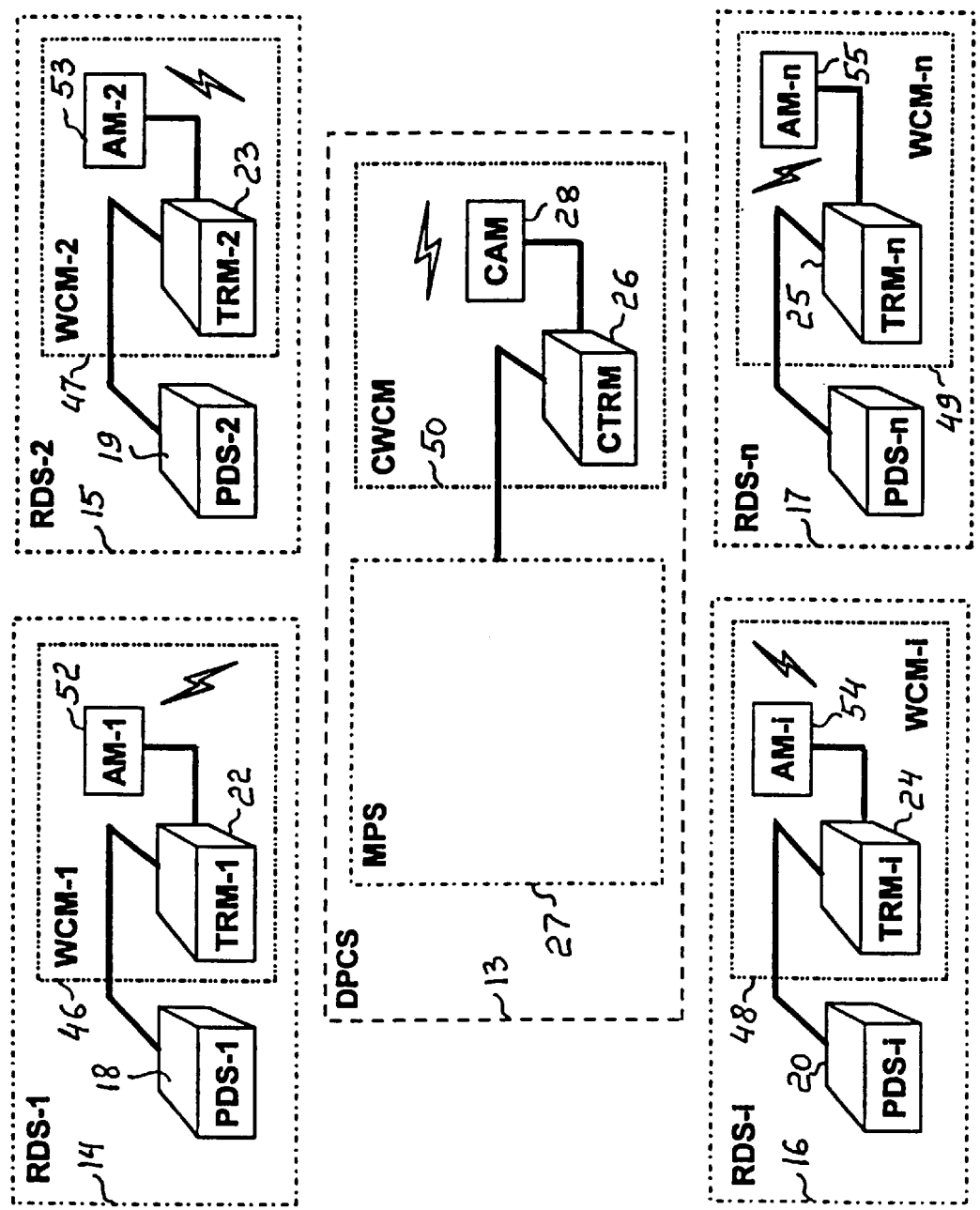
FIG. 10 is a presentation of the simplified structural schematic of an improved wireless communication apparatus (complex).

On FIG. 10 are shown: 13—a data processing and control system; 14—a first remote detecting system (RDS-1); 15—a second remote detecting system (RDS-2); 16—an i-th remote detecting system (RDS-i); 17—a n-th remote detecting system (RDS-n); 18—a particle detecting system the (PDS-1) of the first remote detecting system 14; 19—a particle detecting system (PDS-2) of second remote detecting system 15; 20—a particle detecting system (PDS-i) of the i-th remote detecting system 16; 21—a particle detecting system (PDS-n) of the n-th remote detecting system 17; 22—a transmitting-receiving means (TRM-1) of the first remote detecting system 14; 23—a transmitting-receiving means (TRM-2) of the second remote detecting system 15; 24—a transmitting-receiving means (PDS-i) of the i-th remote detecting system 16; 25—a transmitting-receiving means (PDS-n) of the n-th remote detecting system 17; 26—a central transmitting-receiving means (CORM); 27—a microprocessor system; 28—a central aerial means (CAM); 46—a wireless communication means (WCM-1) of the first remote detecting system 14; 47—a wireless communication means (WCM-2) of the second remote detecting system 15; 48—a wireless communication means (WCM-i) of the i-th remote detecting system 16; 49—a wireless communication means(WCM-n) of the n-th remote detecting system 17; 50—a central wireless communication means (CWCM); 52—an aerial means (AM-1) of the first remote detecting system 14; 53—an aerial means (AM-2) of the second remote detecting system 15; 54—an aerial means (AM-i) of the i-th remote detecting system 16; 55—an aerial means (AM-n) of the n-th remote detecting system 17.

SUMMARY OF THE INVENTION

The invention provides a methods and wireless communicating apparatus particle counting and measuring, having a wireless communication means, intended for two-way communication of the remote particle detecting system(s) with a data processing and control system.

The improved method and device of the particle analyzing provide an airborne (gas) particle and/or liquid contamination counting and measuring, eliminating an analog comparison of the detected signal amplitudes with the appropriate reference voltages and also eliminating the wire (cable), connecting the particle detection system to the data processing and control system. An improved apparatus, realizing the improved methods, includes a remote detecting system, comprising a particle detecting system and a wireless communication means of the remote detecting system, and a data processing and control system, comprising a microprocessor system and a wireless communication means of the data processing and control system. The control signals from a data processing and control system are transmitted by the two-way wireless communication means of the remote data processing and control system to the two-way wireless communication means of the remote detecting system. Further the signals from two-way wireless communication means of the remote detecting system via the appropriate conversion means of the remote detecting system follow to the control means. The control means provide a control (for example, switching operations) of the environment assaying control means (for example, air/liquid pumps, flowmeter, etc.), which by tubular means transfer an assayed composition to the detection means.

The detected signals are amplified, converted to the digital pulse form and strobed by strobe pulses. The selecting, sorting and counting means select and sorts the strobe pulse packages by strobe pulse quantity inside each package and also counts quantity of the strobe pulses within the strobe pulse package (particle size) and quantity of the identical packages (particle quantity).

The initially processed detected signals, containing an information about particle characteristics (size and quantity), are conversed in the data, which is transmitted by two-way wireless communication means of the remote detecting system to the wireless communication means of the remote data processing and control system. Further the signals from two-way communication means of the remote data processing and control system via the appropriate conversion means of the remote data processing and control system follow to the microprocessor system for data processing. The processed data is indicated to the operator in the informative form by terminal means (for example, by a display means or by a printing means).

DESCRIPTION OF THE PREFERRED EMBODIMENTS

Here the description of an improved apparatus will be done in statics (as if the components of the improved apparatus are suspended in the space) with description of their relative locations and connections to each other. The description of the improved methods and functional operations of an improved apparatus will be done hereafter.

FIG. 3 illustrates a structure of the wireless communicating apparatus (for counting and measuring particles), including a remote detecting system 5, having a particle detecting system 4 connected to a wireless communication means 36 of the remote detecting system 5, and a data processing and control system 13, having a microprocessor system 27 connected to a wireless communication means 56 of the data processing and control system 13.

FIG. 4 presents the detailed block-schematic of the wireless communicating apparatus for counting and measuring particles, comprising a remote detecting system 5, which includes a particle detecting system 4 and a wireless communication means 36, having an aerial means 34 connected to a transmitting-receiving means 3. The transmitting-receiving means 3 is connected to a particle detecting system 4. Also the wireless communicating apparatus for counting and measuring particles comprises a data processing and control system 13, which includes a wireless communication means 56 and microprocessor system 27, having a microprocessor means 6, a conversion means 39 and terminal means 38. The wireless communication means 56 includes an aerial means 57 connected to a transmitting-receiving means 58. The transmitting-receiving means 58 connected to the conversion means 39 of the microprocessor system 27. The terminal means 38 can include a displaying means 8, a floppy disk means 9, a compact disk means 10, a printing means 11 and a control panel 12 (for example, a keyboard), which are connected to each other, to the microprocessor means 6 and to the conversion means 39 by a multiplexed bus 7 (can be used a data bus and an address bus, which are not shown).

Referring to FIG. 5, the remote detecting system (sensor) 5 comprises a particle detecting system 4, having a particle detecting means 33 connected to a signal processing system 32, which is connected to a conversion system 31. Also the remote detecting system 5 comprises a wireless communication means 36, having an aerial means 34 connected to a transmitting means 29 and to a receiving means 30 of the transmitting-receiving means 3. The conversion means 31 of the particle detecting system 4 is connected to the transmitting means 29 and to receiving means 30.

FIG. 6 illustrates the detailed block-schematic of the particle detecting system 4, which comprises a conversion system 31, having a conversion means 64 and a coding-decoding means 51 connected either by a multiplexed bus 59 (can be used a data bus and an address bus—not shown), if the conversion means 64 comprises a buffered memory means (not shown), or by a regular connection, as it is shown on FIG. 7. Also the particle detecting system 4 comprises a signal processing system 32 and a particle detecting means 33. The signal processing system 32 includes a detected signal processing means 42 connected to a signal processing means 44, which is connected to a control signal conversion means 45 and to the coding-decoding means 51 of the conversion system 31. The control signal conversion means 45 is connected to a control means 43 and to the coding-decoding means 51 of the conversion system 31. The particle detecting means 33 includes a detection means 40, connected to the detected signal processing means 42 of the signal processing system 32, and an environment assaying control means 41, which is connected to the control means 43 of the signal processing system 32 and to the signal processing means 44 of the signal processing system 32. Also the environment assaying control means 41 is coupled to the detection means 40 by a tubular means 37.

FIG. 7, as it has been mentioned of the above (see description of the FIG. 6), presents a regular connection (not by a bus) of the conversion means 64 and the coding-decoding means 51 of the conversion system 31.

On FIG. 8 is shown the improved apparatus portion, which realizes the signal timing (digital) processing. Referring to FIG. 8, a light detecting means 67 of the detecting system 68, belonging to the detection means 40, is connected to a current-voltage conversion means 69 (if the primer signals light of the detecting means are presented in the current value). The current-voltage conversion means 69 of the detected signal processing means 42 via an amplifying means 70 is connected to a voltage-pulse duration conversion means 71, which is connected to a conjunction means 72 of the signal processing means 44. The strobe pulse generating means 73 is also connected to the conjunction means 72, which is connected to a selecting, sorting and counting means 74.

Figure 9:
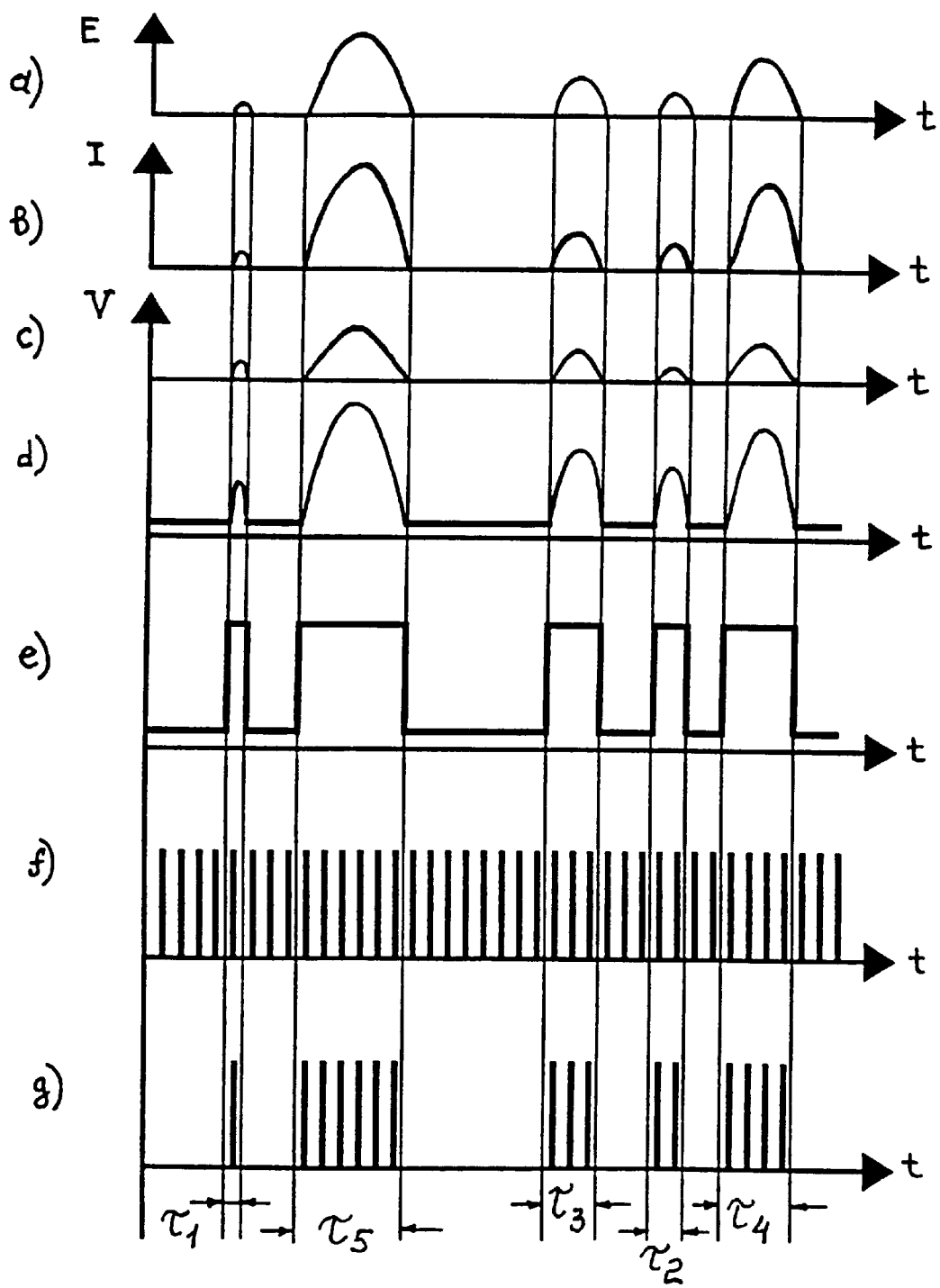
FIG. 9 is a timing diagram.

FIG. 9 presents a timing diagram of the detected signal processing steps, which will be described hereafter.

On the FIG. 10 is presented a structural schematic of the wireless communicating complex for particle counting and measuring, which comprises at least one of a plurality ("N" of (where N=1, 2, ..., i, ..., n) of remote detecting systems and at least one of a plurality of remote data processing and control system. "N" remote detecting systems are presented on FIG. 10 by: a first remote detecting system 14 (RDS-1), a second remote detecting system 15 (RDS-2), an i-th remote detecting system 16 (RDS-i) and a n-th remote detecting system 17 (RDS-n). A plurality of remote data processing and control systems is presented on FIG. 10 by a single remote data processing and control system 13. The first remote detecting system 14 includes a wireless communication means 46, having a transmitting-receiving means 22 connected to an aerial means 52, and a particle detecting system 18 connected to the transmitting-receiving means 22. The second remote detecting system 15 includes a wireless communication means 47, having a transmitting-receiving means 23 connected to an aerial means 53, and a particle detecting system 19 connected to a transmitting-receiving means 23. The i-th remote detecting system 16 comprises a wireless communication means 48, including a transmitting-receiving means 24 connected to an aerial means 54, and a particle detecting system 20 connected to the transmitting-receiving means 24. The n-th remote detecting system 17 includes a wireless communication means 49, comprising a transmitting-receiving means 25 connected to an aerial means 55, and a particle detecting system 21 connected to the transmitting-receiving means 25. The data processing and control system 13 includes a wireless communication means (a central wireless communication means) 50, having a transmitting-receiving means (a central transmitting-receiving means) 26 connected to an aerial means (a central aerial means) 28, and a microprocessor system 27, which is connected to the transmitting-receiving means 26.

The improved methods of counting and measuring particles provides a wireless transmitting of the control signals from the data processing and control system to the remote detecting system and a wireless transmitting of the data (information), characterizing the detected particle parameters, from a remote detecting system to a data processing and control system.

An improved apparatus operates as follows. The wireless communicating apparatus for analyzing of particles (see FIGS. 3, 4, 10) can operate in the three modes: handle service of the data processing and control system 13 by the operator, using a control panel 12 (see FIG. 4) of the terminal means 38 of the data processing and control system 13; automatically by a priori programed stages, conditions, regimes and schedule of the operation and/or recorded, for example, on the floppy disk means 9, or on the compact disk means 10 of the microprocessor system 27, or in E-PROM (not shown) of the microprocessor means 6; and the third mode is the different variations of the handle and automatic modes combination.

Regarding the handle mode of the operation, the operator selects the regimes (for example, by control panel 12 from the menu on the displaying means 8) for remote detecting system 5 operation. The control signals from the control panel 12 (see FIG. 4) of the terminal means 38 follow by the multiplexed bus 7 to the microprocessor means 6 of the microprocessor system 27. Referring to automatic mode of the operation, the regimes are selected either by a floppy disk means 9, or by compact disk means 10, or by E-PROM (not shown) and follow by same multiplexed bus 7 to the microprocessor means 6.

Thus, the control signal, processed by microprocessor means 6, via the conversion means 39 of the microprocessor system 27 follow to the transmitting-receiving means 58 of the wireless communication means 56. The control signal can provide, for example, possibility to switch "on/off", to switch "run/stop", to select and change the particle counting and measuring channels, to provide remote sensor diagnostics, to switch the mode (regime) from particle counting and measuring to concentration determination, to select and change the modes for the particle flow velocity, environmental temperature and/or humidity determination, etc. The signals from the transmitting-receiving means 58 follow to the aerial means 57. The two-way wireless communication means 56 of the remote data processing and control system 13 communicates with the two-way wireless communication means 36 of the remote detecting system 5 (see FIGS. 3, 4) and the signal from the aerial means 57 are received by the aerial means 34 (see FIG. 4) of the wireless communication means 36 and follow via the receiving means 30 of the transmitting-receiving means 3 to the conversion system 31 of the particle detecting system 4, as shown on FIG. 5.

Also referring to FIG. 5, the signals from conversion system 31, including a conversion means 64 and a coding-decoding means 51, follow to the particle detecting means 33 via the signal processing system 32. The conversion system 31 provides the conversion of the received signals to the form, acceptable for further processing. Hereby, the signals from the receiving means 30 follow to the conversion means 64, wherein they can be conversed to the digital form intended, for example, for the further use either the multiplexed bus 59, as it is shown on FIG. 6 or the regular connection, as shown on FIG. 7. Thereby, the conversed signals from the conversion means 64 follow to the coding-decoding means 51 (see FIG. 6). The decoded signals in the digital form from the coding-decoding means 51 follow to the signal processing means 44 and to the control signal conversion means 45, wherein the control signals are conversed to the form required for the control means 43 operation (for example, low power switching means—not shown).

The control means 43 can perform for example, the low power switching functions for the control of the power executive means (not shown) of the environment assaying control means 41 (for example, switching on/off the pump, blower, chamber purging means; switching of the particle size rate means, particle flow control means, etc.—not shown). The assaying air or liquid (water) sample follows by the tubular means 37 from the environment assaying control means 41 to the detection means 40 of the particle detecting means 33.

The particles are detected by the light detecting means 67 of the imaging, or non-imaging means (not shown) of the light detecting system 68 of the detection means 40, belonging to the particle detecting means 33 (see FIG. 8). For example, for fight detecting system 68, using the scattered light detection principles, the signals from light detecting means 67 can be presented by FIG. 9b, where shown the simplified timing diagram I=$f_1$ (t), where: I—an output current of the light detecting means 67 if the primer signals from the light detecting means 67 are the current value signals, t—a time. Regarding the primer detected signals, presented on FIG. 9b, an equation I=$f_2$ (E, $F_1$) should be considered too. In this equation: E—a light intensity (a positive polarity of the signals on FIGS. 9a, 9b is inherent for scattered light detecting principles, but for some other light detecting principles if can be negative or can have the different form), $F_1$—a physical-technical parameters of the light detecting means 67. Referring to FIG. 9a, the primer signals I=$f_1$ (t) from the light detecting means 67 depend on the light intensity E, which can be presented by a function E=$f_3$ (P, D, $F_2$), where: P—a light beam power, D—a particle dimensions (sizes), $F_2$—the other factors (for example, a particle reflectiveness, a particle permeability, etc.). On FIG. 9a is shown the simplified timing diagram E=$f_4$ (t).

The signals (FIG. 9b) from the light detecting means 67 follow to the current-voltage conversion means 69, where they are conversed to the voltage value signals (FIG. 9c), and after the amplifying (FIG. 9d) by an amplifying means 70 they follow to the analog-digital form pulse duration conversion means 71. From the analog-digital form pulse duration conversion means 71 the signals (FIG. 9e) follow to the conjunction means 72, in which also follow strobe pulses (FIG. 9f) from the strobe pulse generating means 73. The signals (FIG. 9g) from the conjunction means 72, having the strobe pulse packages configuration, follow to the selecting, sorting and counting means 74.

The selecting, sorting and counting means 74 provides selection and sorting of the identical strobe pulse packages (packages within the same strobe pulse quantity, that means—with the same strobe pulse package duration $T_i$, where i=0, 1, 2, . . . , k, . . . , n) and also provides the counting of the identical strobe pulse packages (particle quantity) and the counting of the strobe pulse quantity in the mentioned packages (particle size). The $T_i$ characterizes the particle sizes. The more strobe pulses within a strobe pulse package (the larger value of $T_i$), the bigger particle size. The higher frequency of the strobe pulses, the higher precision and sensitivity of an improved apparatus. The signals, containing information about particle characteristics, from the selecting, sorting and counting means 74 follow to the constituent parts (blocks) of the signal processing means 44, in which also follow the signals, containing the information, for example, about environmental temperature, humidity, velocity rate, etc. The signals (for example, the coordinating or synchronizing signals) from the signal processing means 44 follow to the control signal conversion means 45 and to the environment assaying control means 41. Further the processed signals, containing the information about particle quantity and dimensions, follow to the coding-decoding means 51 for coding (see FIG. 6).

The coded data from the coding-decoding means 51 via conversion means 64 follow to the transmitting means 29 of the transmitting-receiving means 3 (see FIG. 5) and further from the transmitting means 3 follow to the aerial means 34 of the wireless communication means 36.

By a wireless communication, the signals, received by the aerial means 57 of the data processing and control system. 13, as shown on FIG. 4, follow to the receiving means (not shown) of the transmitting-receiving means 58 of the wireless communication means 56. The signals from the transmitting-receiving means 58 follow to the conversion means 39 of the microprocessor system 27 and further the conversed signals follow by the multiplexed bus 7 to the microprocessor means 6 for decoding and the received data processing. The processed information (data), containing the characteristics of the assayed environment (air, gas, liquid or water, for instance), is displayed in the convenient for operator form (e.g., graphics, diagrams, tables, texts, etc.) on the displaying means 8 and/or can be printed by printing means 11.

Referring to FIG. 10, an improved apparatus can comprise N=1, 2, . . . , i, . . . , n remote detecting systems and, for example, at least one data processing and control system. The wireless communication process is the same as described of the above, but the remote data processing and control system 13 serves "N" remote detecting systems (on FIG. 10 "N" remote detecting systems are presented by 14, 15, 16, 17). Regarding FIG. 10, each remote detecting system 14, 15, 16, 17 includes the appropriate particle detecting system 18, 19, 20, 21 and the appropriate wireless communication means 46, 47, 48, 49, having the appropriate transmitting-receiving means 22, 23, 24, 25 and appropriate aerial means 52, 53, 54, 55. Each remote detecting system has the conventional address (code) for the wireless communication, which is recognized by the coding-decoding means included in the conversion system of the each remote detecting system (see, for example, FIGS. 6, 7) and by the microprocessor system 27 of the data processing and control system 13. Therefore, each remote detecting system operates independently of each other. The data processing and control system 13 communicates with the remote detecting systems 14, 15, 16, 17 by central wireless communication means 50, comprising the central transmitting-receiving means 26 and the central aerial means 28.

The wireless communication can be provided by at least one-way wireless communication from the remote detecting system to the data processing and control system, if the remote detecting system includes a programmable means (not shown), or built-in some control means (not shown), or if remote detecting system can work in the permanent predetermined regimes.

Also, the mentioned above wireless communication means and also aerial means, transmitting-receiving mean, transmitting means and receiving means (not shown on FIG. 10) can be an identical (can have the same performance).

CONCLUSION, RAMIFICATION AND SCOPE

Accordingly the reader will see that, according to the invention, I have provided an effective methods and apparatus, which provide counting and measuring of the particles of the assayed air (gas) or liquid contaminations.

An improved method and apparatus provide authenticity of the quantity and sizes of the particles in the assayed mixture of air or liquid, because the electromagnetic noise created in the known prior art by wire (electrical cable) connection of the particle detecting means to the data processing means, is eliminated in an improved apparatus.

Also an improved method and apparatus provide the maximal mobility of the remote sensor. This factor may be very convenient for the improved apparatus use in the difficult accessible areas, where the operator's activity or the cable (wire) tracing cannot be used.

Additionally, an improved method of the detected signal timing processing, and apparatus provide the increasing of the sensitivity. An improved method makes it possible to achieve sensitivity much less than 0.1 $\mu m$.

While the above description contains many specificities, these should not construed as limitations on the scope of the invention, but as exemplification of the presently-preferred embodiments thereof. Many other ramifications are possible within the teaching of the invention. For example, an improved method and apparatus provide a maximal portability of the wireless communicating remote detecting system.

Thus, the scope of the invention should be determined by the appended claims and their legal equivalents, and not by examples given.

What is claimed is:

1. A method for counting and measuring particles illuminated by a light beam, providing two-way wireless communication between a data processing and control system and a remote particle detecting system, said method comprising the steps of:

forming in said data processing and control system at least one of control signals, which provide a turning-on, turning-off and switching of modes of operation of said remote particle detecting system;

conversing said control signals to the form for wireless transmission;

wireless transmitting of the conversed control signals from said data processing and control system to said remote particle detecting system;

wireless receiving of the transmitted control signals by said remote particle detecting system;

conversing the received control signals to the form for control of said remote particle detecting system;

sensing by a light detecting means of a particle detecting means of said remote particle detecting system a light created by an intersection of said light beam and said particles within a particle monitoring region and providing an output, which is effectively indicative of a size of said particles;

processing said output by a signal processing system of said remote particle detecting system;

forming in said signal processing system of said remote detecting system a data, containing an information about a quantity and said size of said particles;

conversing said data, containing said information about said quantity and said size of said particles to the form for wireless transmission;

wireless transmitting of the conversed data, containing said information about said quantity and said size of said particles, from said remote particle detecting system to said data processing and control system;

wireless receiving of the transmitted data, containing said information about said particle quantity and size, by said data processing and control system;

conversing the received data, containing said information about said quantity and said size of said particles to the form for processing;

processing the conversed data, containing said information about said quantity and said size of said particles, by said data processing and control system.

2. The method of claim 1, wherein said two-way wireless communication is provided by a transmitting-receiving means of a wireless communication means of said remote particle detecting system via an aerial means of said wireless communication means of said remote particle detecting system and by an adequate transmitting-receiving means of an adequate wireless communication means of said data processing and control system via an adequate aerial means of said adequate wireless communication means of said data processing and control system.

3. An apparatus for counting and measuring particles illuminated by a light beam, providing two-way wireless communication between a data processing and control system and remote particle detecting systems, said apparatus comprises:

at least on of a plurality of said wireless communicating remote particle detecting systems, each of which includes a particle detecting system, comprising a particle detecting means, including detection means, comprising a light detecting means of a light detecting system;

a signal processing system, providing a processing of an output from said light detecting system and forming a data, containing an information about a quantity and a size of said particles;

a conversion system, converting control signals, received from said data processing and control systems, to the form for control of said remote particle detecting system and converting said data, containing said information about said quantity and said size of said particles, to the form for transmission to said data processing and control systems;

a wireless communication means, comprising
- a wireless transmitting-receiving means, including a transmitting means, providing the transmission of said data, containing said information about said quantity and said size of said particles, to said data processing and control system, and a receiving means, providing the receiving of said control signals from said data processing and control system; and
- an aerial means;

at least one said wireless communicating data processing and control system, comprising a processing system, including
- a microprocessor means, forming said control signals and processing said data received from said remote particle detecting system and containing said information about said quantity and said size of said particles;
- a terminal means, comprising at least one of: a displaying means, a floppy disk means, a compact disk means, a printing means and a control panel; and
- a conversion means, converting said control signals to the form for transmission to said remote particle detecting system and converting said data received from said remote particle detecting system to the form for processing by said processing system;

an adequate wireless communication means, including
- an adequate wireless transmitting-receiving means, comprising an adequate transmitting means, providing the transmission of said control signals to said remote particle detecting system, and an adequate receiving means, providing the receiving of said data, containing said information about said quantity and said size of said particles, from said remote particle detecting system; and
- an adequate aerial means.

4. The apparatus of claim 3, wherein said particle detecting means of each of said wireless communicating remote particle detecting systems includes a tubular means coupling a detection means and an environment assaying control means.

5. The apparatus of claim 3, wherein said conversion system of each of said wireless communicating remote particle detecting systems includes an appropriate conversion means connected to a coding-decoding means, providing recognition of a conventional identification number of an appropriate wireless communicating remote particle detecting system.

6. An apparatus for counting and measuring particles, providing a processing of an output of a light detecting means, said apparatus comprises:
- a current-voltage conversion means, providing conversion of said output of said light detecting means to voltage value signals, and wherein said output is effectively indicative of a size of said particles;
- an amplifying means, providing an amplification of said voltage value signals;
- an analog-digital form pulse duration conversion means, providing conversion of each of said voltage value signals to digital form pulses, and wherein each of said digital form pulses has a duration, which is adequate to the duration of an appropriate output of said light detecting means;
- a strobe pulse generating means, providing generating of strobe pulses;
- a conjunction means, forming a strobe pulse packages by conjunction of each of said digital form pulses and said strobe pulses;
- a selecting, sorting and counting means, providing the selection and sorting of said strobe pulse packages by an identical quantity of said strobe pulses within each of said strobe pulse packages.

7. The apparatus of claim 6, wherein said amplifying means is connected to said light detecting means through said current-voltage conversion means, and wherein said analog-digital form pulse duration conversion means is connected to said amplifying means.

8. The apparatus of claim 6, wherein said conjunction means is connected to said analog-digital form pulse duration conversion means, to said strobe pulse generating means and to said selecting, sorting and counting means.

* * * * *

UNITED STATES PATENT AND TRADEMARK OFFICE
CERTIFICATE OF CORRECTION

PATENT NO. : 6,346,983 B1
DATED : February 12, 2000
INVENTOR(S) : Aleksandr L. Yufa It is certified that error appears in the above-identified patent and that said Letters Patent is hereby corrected as shown below:

<u>Title page, Item [54] and Column 1, line 1,</u>
Title, change "METHODS" to -- METHOD --.

Item [57], ABSTRACT,
Line 1, change "methods" to -- method --.

<u>Drawings,</u>
Fig.2 (a prior art), change "20" to -- 35 -- and change "22" to -- 75 -- and change "24 (12)" to -- 76 --.

<u>Column 2,</u>
Line 11, change "intersecting" to -- particles crossing the laser beam --.
Line 29, delete "light the sufficiently light".
Line 30, change "the sensitivity" to -- the sufficient sensitivity --.
Line 38, change "detecting, means" to -- detecting means --.
Line 49, change "20" to -- 35 --.
Line 50, change "22" to -- 75 -- and "24(12)" to -- 76 --.

<u>Column 3,</u>
Line 26, change "and" to -- and data processing means (computers) --.
Line 28, change "such" to -- the long --.
Line 29, change ", using" to -- used --.
Line 30, delete "with the known devices".

<u>Column 4,</u>
Line 21, change "providing a" to -- providing the --.
Line 22, change "timing a strobing processes" to -- processing of the initial signals --.
Line 25, change "communication" to -- communicating --.

<u>Column 5,</u>
Line 7, delete "ted".
Line 22, change "analog digital" to -- analog-digital --.
Line 30, change "system the" to -- system --.
Line 58, change "apparatus particle" to -- apparatus for particle --.

<u>Column 6,</u>
Lines 34, 35 and 37, delete "remote".

<u>Column 7,</u>
Line 59, delete "light".
Line 62, change "voltage-pulse" to -- voltage (analog)-digital form pulse --.

UNITED STATES PATENT AND TRADEMARK OFFICE
CERTIFICATE OF CORRECTION

PATENT NO. : 6,346,983 B1
DATED : February 12, 2000
INVENTOR(S) : Aleksandr L. Yufa It is certified that error appears in the above-identified patent and that said Letters Patent is hereby corrected as shown below:

<u>Column 8,</u>
Line 5, change " ("N" " to -- "N" --.
Line 6, change "of (where" to -- (where --.
Line 7, delete "remote".

<u>Column 9,</u>
Line 16, delete "remote".
Line 58, change "fight" to -- light --.

<u>Column 10,</u>
Line 2, change "if" to -- it --.
Line 24, change "within" to -- with --.

<u>Column 11,</u>
Line 3, delete "remote".

<u>Column 12,</u>
Line 39, change "and size" to -- and said size --.
Line 62, change "at least on of" to -- at least one of --.

Signed and Sealed this

Twenty-second Day of October, 2002

*Attest:*

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO.    : 6,346,983 B1                                             Page 1 of 2
DATED         : February 12, 2002
INVENTOR(S)   : Aleksandr L. Yufa It is certified that error appears in the above-identified patent and that said Letters Patent is hereby corrected as shown below:

<u>Title page, Item [54] and Column 1, line 1,</u>
Title, change "METHODS" to -- METHOD --.

Item [57], ABSTRACT,
Line 1, change "methods" to -- method --.

<u>Drawings,</u>
Fig. 2, (a prior art), change "20" to -- 35 -- and change "22" to -- 75 -- and change "24 (12)" to -- 76 --.

<u>Column 2,</u>
Line 11, change "intersecting" to -- particles crossing the laser beam --.
Line 29, delete "light the sufficiently light".
Line 30, change "the sensitivity" to -- the sufficient sensitivity --.
Line 38, change "detecting, means" to -- detecting means --.
Line 49, change "20" to -- 35 --.
Line 50, change "22" to -- 75 -- and "24(12)" to -- 76 --.

<u>Column 3,</u>
Line 26, change "and" to -- and data processing means (computers) --.
Line 28, change "such" to -- the long --.
Line 29, change ", using" to -- used --.
Line 30, delete "with the known devices".

<u>Column 4,</u>
Line 21, change "providing a" -- to providing the --.
Line 22, change "timing a strobing processes" to -- processing of the initial signals --.
Line 25, change "communication" to -- communicating --.

<u>Column 5,</u>
Line 7, delete "ted".
Line 22, change "analog digital" to -- analog-digital --.
Line 30, change "system the" to -- system --.
Line 58, change "apparatus particle" to -- apparatus for particle --.

<u>Column 6,</u>
Lines 34, 35 and 37, delete "remote".

<u>Column 7,</u>
Line 59, delete "light".
Line 62, change "voltage-pulse" to -- voltage (analog)-digital form pulse --.

UNITED STATES PATENT AND TRADEMARK OFFICE
CERTIFICATE OF CORRECTION

PATENT NO.    : 6,346,983 B1
DATED         : February 12, 2002
INVENTOR(S)   : Aleksandr L. Yufa It is certified that error appears in the above-identified patent and that said Letters Patent is hereby corrected as shown below:

Column 8,
Line 5, change " ("N" " to -- "N" --.
Line 6, change "of (where" to -- (where --.
Line 7, delete "remote".

Column 9,
Line 16, delete "remote".
Line 58, change "fight" to -- light --.

Column 10,
Line 2, change "if" to -- it --.
Line 24, change "within" to -- with --.

Column 11,
Line 3, delete "remote".

Column 12,
Line 39, change "and size" to -- and said size --.
Line 62, change "at least on of" to -- at least one of --.

This certificate supersedes Certificate of Correction issued October 22, 2002.

Signed and Sealed this

Twenty-first Day of January, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,346,983 B1  
DATED : February 12, 2002  
INVENTOR(S) : Aleksandr L. Yufa It is certified that error appears in the above-identified patent and that said Letters Patent is hereby corrected as shown below:

Column 6,  
Line 30, change "conversed" to -- converted --.

Column 9,  
Lines 32 and 35, change "conversed" to -- converted --.  
Line 41, change "versed" to -- verted --.

Column 10,  
Line 59, change "conversed" to -- converted --.

Column 12,  
Line 9, change "turning-off" to -- turning-off, --.  
Lines 11, 18, 31 and 41, change "conversing" to -- converting --.  
Lines 13, 34 and 44, change "conversed" to -- converted --.

Signed and Sealed this

Twenty-eighth Day of March, 2006

JON W. DUDAS  
*Director of the United States Patent and Trademark Office*

US006346983C1

(12) EX PARTE REEXAMINATION CERTIFICATE (9186th)
United States Patent
Yufa

(10) Number: US 6,346,983 C1
(45) Certificate Issued: Aug. 14, 2012

(54) METHOD AND WIRELESS COMMUNICATING PARTICLE COUNTING AND MEASURING APPARATUS

(75) Inventor: Aleksandr L. Yufa, Colton, CA (US)

(73) Assignee: Aleksandr L. Yufa, Colton, CA (US)

Reexamination Request:
No. 90/008,387, Dec. 21, 2006

Reexamination Certificate for:
Patent No.: 6,346,983
Issued: Feb. 12, 2002
Appl. No.: 09/015,458
Filed: Jan. 29, 1998

Certificate of Correction issued Oct. 22, 2002.

Certificate of Correction issued Jan. 21, 2003.

Certificate of Correction issued Mar. 28, 2006.

(51) Int. Cl.
*G01N 15/14* (2006.01)

(52) U.S. Cl. .......... 356/338
(58) Field of Classification Search .......... 702/127, 702/182
See application file for complete search history.

(56) References Cited

To view the complete listing of prior art documents cited during the proceeding for Reexamination Control Number 90/008,387, please refer to the USPTO's public Patent Application Information Retrieval (PAIR) system under the Display References tab.

*Primary Examiner* — B. James Peikari

(57) ABSTRACT

An improved method and apparatus for particle counting and measuring provide the counting and measuring of the airborne (gas) particle and/or liquid contamination and include a remote sensor 5, wireless communicating with a data processing and control system 13, comprising a microprocessor system 27 and a wireless communication means 56, comprising a transmitting-receiving means 58 connected to an aerial means 57. The sensor system 5 includes a particle detecting system 4, providing the sensing a light created by an intersection of the particles with a light beam within particle monitoring region of the particle detecting system 4, particle detection and timing processing of the detected signals, and a wireless communication means 36 intended for wireless communication with the data processing and control system 13, providing a received data processing, illuminating of the resulting information and also providing a wireless communicating control of the sensor 5.

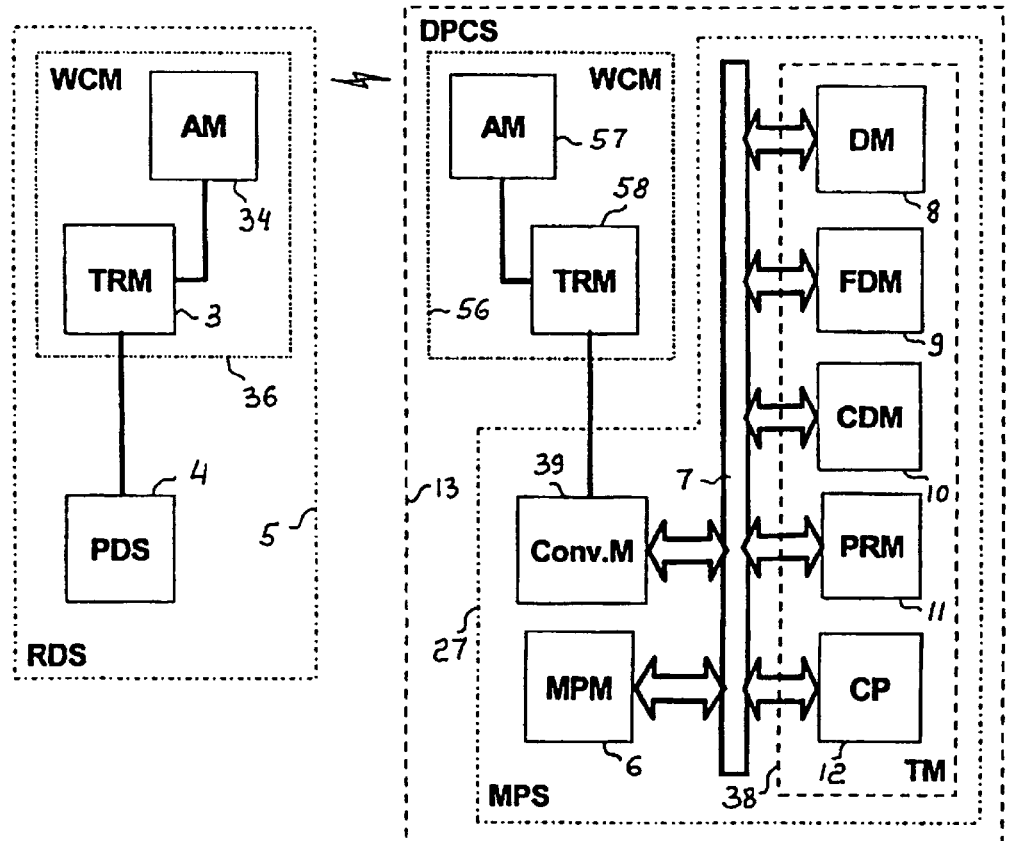

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-5 are cancelled.

Claims 6-8 are determined to be patentable as amended.

6. An apparatus for counting and measuring particles, providing a processing of an output of a light detecting means, said apparatus comprises:
   a current-voltage conversion means, providing conversion of said output of said light detecting means to voltage value signals, and wherein said output is effectively indicative of a size of said particles;
   an amplifying means, providing an amplification of said voltage value signals;
   an analog-digital form pulse duration conversion means, providing conversion of each of said voltage value signals to *a* digital form [pulses, and] *pulse without using a reference voltage to convert each of said voltage value signals*, wherein each [of] said digital form [pulses] *pulse* has a duration, which is adequate to [the duration of an] *a baseline duration of the* appropriate output of said light detecting means;
   a strobe pulse generating means, providing generating of strobe pulses;
   a conjunction means, forming [a] strobe pulse packages by conjunction of [each of] *each* said digital form [pulses] *pulse* and said strobe pulses;
   a selecting, sorting and counting means, providing the selection and sorting of said strobe pulse packages by an identical quantity of said strobe pulses within each of said strobe pulse packages.

7. The apparatus of claim 6, wherein said amplifying means is connected to said light detecting means through said current-voltage conversion means and [wherein] *to* said analog-digital form pulse duration conversion [means is connected to said amplifying means] *means*.

8. The apparatus of claim 6, wherein said conjunction means is connected [to said analog-digital form pulse duration conversion means,] to said strobe pulse generating [means and] *means*, to said selecting, sorting and counting means, *and to said analog-digital form pulse duration conversion means*.

* * * * *